US012440132B2

(12) United States Patent
Rahmati

(10) Patent No.: US 12,440,132 B2
(45) Date of Patent: Oct. 14, 2025

(54) WASTE TUBE CARTRIDGE FOR PHLEBOTOMY

(71) Applicant: Kasra Rahmati, Salt Lake City, UT (US)

(72) Inventor: Kasra Rahmati, Salt Lake City, UT (US)

( * ) Notice: Subject to any disclaimer, the term of this patent is extended or adjusted under 35 U.S.C. 154(b) by 1026 days.

(21) Appl. No.: 17/101,937

(22) Filed: Nov. 23, 2020

(65) Prior Publication Data

US 2021/0282683 A1 Sep. 16, 2021

Related U.S. Application Data

(60) Provisional application No. 62/988,257, filed on Mar. 11, 2020.

(51) Int. Cl.
*A61B 5/15* (2006.01)

(52) U.S. Cl.
CPC .. *A61B 5/150206* (2013.01); *A61B 5/150236* (2013.01); *A61B 5/150343* (2013.01)

(58) Field of Classification Search
None
See application file for complete search history.

(56) References Cited

U.S. PATENT DOCUMENTS

| | | | | |
|---|---|---|---|---|
| 4,150,666 A | | 4/1979 | Brush | |
| 4,320,769 A | | 3/1982 | Eichhorn et al. | |
| 4,325,369 A | * | 4/1982 | Nilson | A61M 5/282 604/403 |
| 4,931,040 A | * | 6/1990 | Haber | A61M 5/322 604/110 |
| 6,083,199 A | * | 7/2000 | Thorley | A61M 5/3234 604/110 |
| 2008/0097338 A1 | * | 4/2008 | Cheng | A61M 5/3129 604/201 |
| 2015/0005669 A1 | * | 1/2015 | Burkholz | A61B 5/150992 600/576 |
| 2016/0324455 A1 | * | 11/2016 | Crosby | A61B 5/150022 |
| 2020/0352498 A1 | * | 11/2020 | Schuster | A61B 5/150259 |

FOREIGN PATENT DOCUMENTS

WO WO-2021150398 A1 * 7/2021 ....... A61B 5/150007

* cited by examiner

*Primary Examiner* — Jacqueline Cheng
*Assistant Examiner* — Jairo H Portillo
(74) *Attorney, Agent, or Firm* — Holzer Patel Drennan

(57) ABSTRACT

A cartridge is designed to secure and position a waste tube during a blood draw operation. The cartridge includes a T-shaped body with a tubular central portion and one or more gripping flanges. The tubular central portion has an open first end and an elongated cavity elongated cavity that is sized and shaped to receive the waste tube through the open first end. The one or more gripping flanges are attached to a second end of the tubular central portion opposite the first end and extend out away from the tubular central portion in a plane substantially perpendicular to elongated cavity. The cartridge further includes a plunger mechanism affixed to the T-shaped body. The plunger mechanism includes a stem adapted to slide into the cavity through the second end of tubular central portion responsive to an applied external force to eject the waste tube from the cavity through the open first end of the cavity.

12 Claims, 8 Drawing Sheets

WASTE TUBE CARTRIDGE FOR PHLEBOTOMY

The present application claims priority to provisional application Ser. No. 62/988,257, and filed on Mar. 11, 2020, which is hereby incorporated by reference for all that it discloses or teaches.

BACKGROUND

When drawing blood, a phlebotomist typically uses a blood collection apparatus that includes a needle and a blood collection vial connected to the needle via a first length of tubing. The blood collection apparatus is typically coupled to a waste tube by another length of tubing. The waste tube receives waste that is expelled from the blood collection apparatus as the blood accumulates in the blood collection vial. For example, the waste may include a saline solution and/or air that is initially in the blood collection vial prior to the blood draw. As this waste is displaced by blood, the waste is drawn into waste tube which remains vacuum-sealed throughout the blood draw. Use of the waste tube ensures that the blood collection vial remains free of any potential contaminants. When used correctly, a waste tube may be sterilized post-use and recycled for future use.

In some cases, a hub is used to help attach the waste tube to tubing that extends from the needle to the blood collection vial. The hub may, for example, include a casing that the waste tube rests within to keep the waste tube properly positioned during the blood draw. The casing typically includes a needle that provides a channel into the waste tube when the waste tube is correctly inserted in the hub. This configuration allows for vacuum-sealed transmission of fluids between the blood collection apparatus and the waste tube.

While industry standard, the above-described configuration presents some challenges. Typically, a phlebotomist attaches the waste tube to the hub after inserting the blood draw needle into a vein. Thus, the phlebotomist uses one hand to hold the needle in place within the vein and has only one free hand to insert the waste tube into the hub. If the waste tube is inserted at an angle such that there exists a slight misalignment between an aperture in a rubber tip of the waste tube and the first end of the needle, the needle may puncture the glass side of the waste tube, breaking it and rendering it unusable. In current applications, the waste tube failure rate of this operation is as high as 25-30%. The need to replace rather than reuse nearly ⅓ of all waste tubes directly impacts supply costs for medical facilities. Moreover, since it is relatively easy to accidently break the waste tube, phlebotomists may take extra care during blood draw procedures to correctly attach the waste tube to the hub. This increases the total time of each blood draw operation, reducing overall efficiency. In clinic trials, phlebotomists may be critiqued on their ability to meet per-sample time goals (e.g., collect a number of samples in a set period of time). The high waste tube failure rate and reduced efficiency associated with current designs frustrate these goals.

SUMMARY

According to one implementation, a cartridge for securing a waste tube during a phlebotomy operation has a T-shaped body that includes a tubular central portion and one or more gripping flanges. The tubular central portion has an open first end and an elongated cavity, the elongated cavity being sized and shaped to receive the waste tube through the open first end. The one or more gripping flanges are attached to a second end of the tubular central portion that is opposite the first end and positioned to extend from the tubular central portion in a plane substantially perpendicular to elongated cavity. The cartridge further includes a plunger mechanism affixed to the T-shaped body that includes a stem adapted to slide into the elongated cavity through the second end of tubular central portion responsive to an applied external force to eject the waste tube from the elongated cavity through the open first end of the cavity.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other implementations are also described and recited herein.

DETAILED DESCRIPTION

The technology disclosed herein includes a cartridge that is used to secure a waste tube within a hub during a blood draw. Features of the cartridge simplify coupling of the waste tube and the hub so as to reduce waste tube failure rates, extending the effective lifetime of each waste tube and thereby reducing total supply costs.

Figure 1:
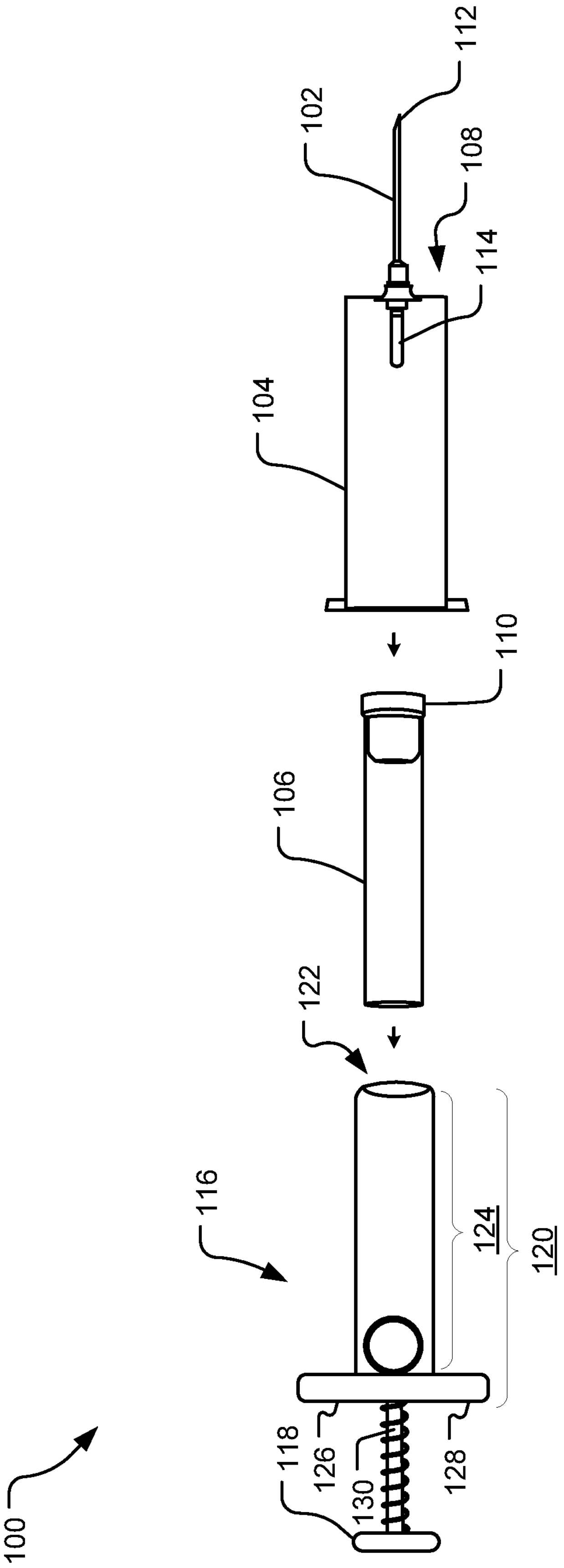
FIG. 1 illustrates an exemplary tool set that may be used to facilitate phlebotomy operations.

FIG. 1 illustrates an exemplary tool set 100 that may be used to facilitate phlebotomy operations. The illustrated tool set 100 include a hub 104, a hub needle 102, and a waste tube 106. The hub needle 102 is positioned partially internal to a first end 108 of the hub 104. During a blood draw, an exposed end 112 of the hub needle 102 may be further attached to tubing and a blood collection vial (not shown) such that the hub needle 102 may be used to draw fluid up and into the waste tube 106 when the waste tube 106 is correctly positioned within the hub 104.

By example and without limitation, the waste tube 106 is shown to include a rubber stopper 110 that is designed to mate with a portion of the hub needle 102 internal to the hub 104. For example, the portion of the hub needle 102 internal to the hub 104 may include a rubber sleeve 114 that is adapted for insertion into a tiny aperture in the rubber stopper 110, such that the rubber sleeve 114 may form an air tight seal against the rubber stopper 110 while allowing fluid to flow up through the needle 102 and into the waste tube 106.

In traditional phlebotomy operations, it can be difficult to properly position the waste tube 106 within the hub 104, particularly if the user has only one free hand (e.g., because the other hand is used to apply pressure to a needle within a vein). If the waste tube 106 is inserted into the hub 104 at a slight angle, the portion of the needle that is internal to the hub 104 may strike and break the glass of the waste tube 106.

In the system of FIG. 1, the foregoing risk is avoided by using a cartridge 116 to hold and secure the waste tube 106 throughout the duration of the blood draw procedure. The use of the cartridge 116 makes it easier to properly align the center of the waste tube 106 with the center of the hub 104, and also facilitates touchless removal of the waste tube 106 from the hub 104, and touchless disposal of the waste tube 106 after the procedure is finished. As used herein, an operation is said to be "touchless" with respect to the waste tube 106 if the operation can be performed without requiring the user to directly touch the waste tube 106. For example, the waste tube 106 may be touchlessly removed from the hub 104 by pulling cartridge 116 out of the hub 104 (without directly touching the waste tube 106) while the waste tube 106 is still secured within the cartridge 116.

In one implementation, the cartridge 116 is designed to remain external to the waste tube 106 and is therefore completely isolated from the fluid channel that draws liquid waste air up the hub needle 102 and into the waste tube 106 such that there is no risk that the cartridge 116 may come into contact with fluids that are flowed into and stored within the waste tube 106. Thus, the cartridge 116 can be readily reused without a need for sterilization between uses.

Although the cartridge 116 may have different features in different implementations, the cartridge 116 of FIG. 1 is shown to include a T-shaped body 120 that includes a tubular central portion 124 with an open first end 122 that provides a mouth to an elongated internal cavity. The elongated internal cavity is sized and shaped to receive the waste tube 106 through the open first end 122. In one implementation, the tubular central portion 124 includes internal features that function to temporarily lock the waste tube 106 into position within the elongated internal cavity. For example, the tubular central portion 124 may include a sidewall with internally-protruding features, such as textured ribs or teeth to provide friction that effectively locks the waste tube 106 into place. Alternatively, some implementations of the cartridge 116 may include a selectively engageable locking mechanism, such as a button that may be pressed to close an internal latch that locks the waste tube 106 into place within the tubular central portion 124.

In addition to the tubular central portion 124, the cartridge 116 further includes gripping flanges 126 and 128 that extend in a direction substantially perpendicular to a primary axis of the tubular central portion 124. As used herein, "substantially perpendicular" shall refer to an angle that is within +/−5% of true perpendicular.

In addition to the features discussed above, the cartridge 116 further includes a plunger mechanism 118 affixed to the T-shaped body 120. The plunger mechanism 118 includes a stem 130 that is adapted to slide in and out of the cavity in the tubular central portion 124 responsive to an external force applied to push the stem 130 toward the cavity. The plunger mechanism 118 is shown to be spring-loaded such that a majority of the stem 130 is external to the cavity in the absence of applied force. When the user applies a force to the plunger mechanism 118, the spring collapses and allows the stem 130 to contact and dislodge the waste tube 106 within the cavity, pushing the waste tube 106 out through the open end 122. For example, the user uses an index and middle finger on one hand to pull the gripping flanges 126, 128 in a first direction while using his/her thumb to force the stem 130 of the plunger mechanism 118 into the cavity, thereby forcibly ejecting the waste tube 106 out through the open end 122. By engaging the plunger mechanism 118 in this way, the waste tube 106 may be selectively dislodged and pushed out of the cartridge without requiring the user to physically touch the waste tube 106.

Figures 2A, 2B:
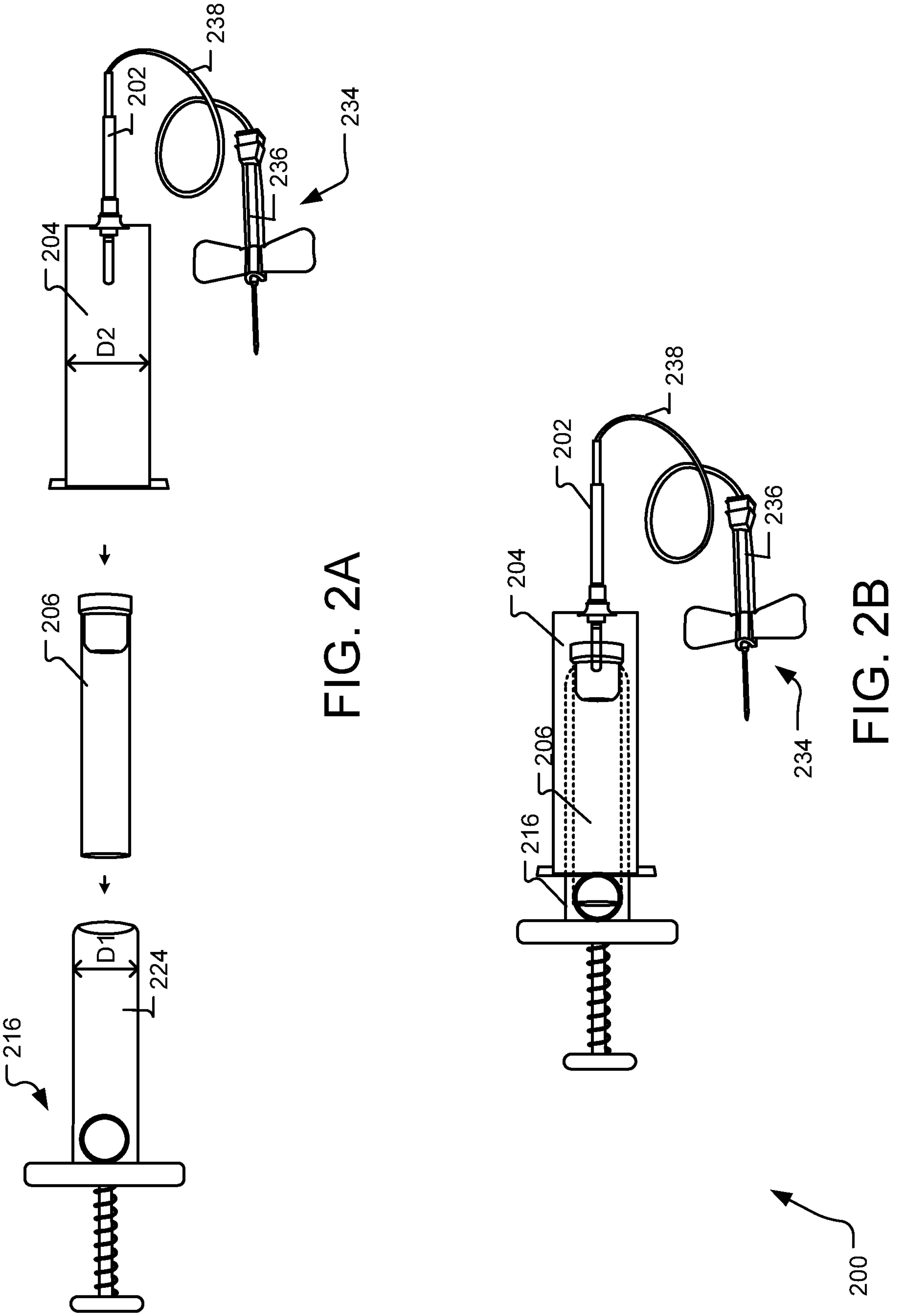
FIG. 2A illustrates aspects of another exemplary tool set that may be used to facilitate phlebotomy operations.
FIG. 2B illustrates the exemplary tool set of FIG. 2A according to an alternate configuration.

FIG. 2A illustrates aspects of another exemplary tool set 200 that may be used to facilitate phlebotomy operations. The illustrated tool set 200 differs from that shown in FIG. 1 in that it is further shown to include a butterfly needle 234 that is used to collect blood from a user's vein. The butterfly needle 234 includes a collection vial 236 that may be initially filled with a saline solution. The butterfly needle 234 is coupled to a hub 204 by a hub needle 202. Prior to a blood draw, a waste tube 206 is inserted into a cartridge 216 that includes features the same or similar to those described above with respect to cartridge 116 of FIG. 1. After the waste tube 206 is positioned within the cartridge 216, a user uses the cartridge 216 to insert the waste tube 206 into the tub 204. The cartridge 216 has a tubular central portion 224 with a diameter D1 that is smaller than but closely matched to a diameter D2 of the hub 204. Thus, the cartridge 216 inserts easily into the hub 204 when correctly aligned. In this case, "correct alignment" implies that a central longitudinal axis of the cartridge 216 is aligned with and parallel to a longitudinal axis of the hub 204. If the central longitudinal axis of the cartridge 216 is at an angle relative to the longitudinal axis of the hub 204, the cartridge 216 cannot be inserted into the hub.

Since the cartridge 216 prevents the needle in the hub 204 from striking the waste tube 206 at an angle (which could potentially shatter the glass tube), use of the cartridge 216 decreases the failure rate of the waste tube 206. Moreover, the cartridge 216 is easy to grip with one hand, thereby improving the ease of connecting the waste tube 206 to the hub 204 and improving the speed of such process.

FIG. 2B illustrates the exemplary tool set 200 after the waste tube 206 has been inserted into the cartridge 216 and the cartridge 216 has been inserted to the hub 204. As shown, the cartridge 216 fits snuggly within the hub 204. The cartridge 216 remains entirely external to the waste tub 206 and does not contact the interface between the hub needle 202 and the waste tube 206. Therefore, the cartridge 216 is not exposed to any potential liquid contaminants (e.g., blood, saline solution) that may flow into the waste tube 206. To remove the waste tube 206 from the hub 204, a user simply pulls the cartridge 216 and the hub 204 in opposing directions. The waste tube 206 remains secure within the cartridge 216 and the cartridge 216 separates from the hub 204.

Figure 3:
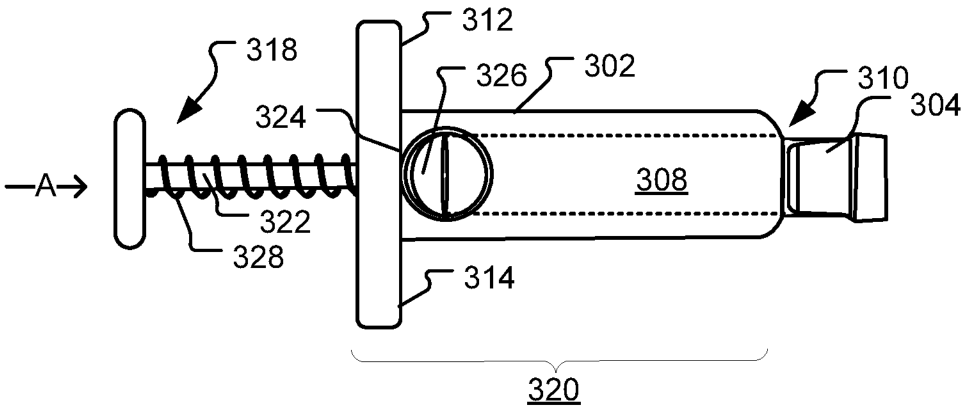
FIG. 3 illustrates an exemplary cartridge used to hold and secure a waste tube during phlebotomy operations.

FIG. 3 illustrates an exemplary cartridge 302 used to hold and secure a waste tube 304. The cartridge 302 includes features the same or those similar to FIG. 1-2 above including a T-shaped body 320 and a plunger mechanism 318. The T-shaped body 320 includes a tubular central portion 308 that has an opening on a first end 310 and central elongated cavity (not shown) that receives the waste tube 304 through the open first end 310. The central elongated cavity is sized and shaped to receive the waste tube 304 through the open first 310.

Although not shown in FIG. 3, the cartridge 302 may include inwardly-protruding gripping structures (e.g., ridges, teeth, or other structures internal to the central elongated cavity) that are designed to provide a frictional force that grips the waste tube 304 in place within the central elongated cavity. For example, the waste tube 304 may easily slide into the central elongated cavity through the open first end 310 and encounter some frictional resistance upon reaching a portion of the central elongated cavity that includes the gripping structures. This resistance is small enough that the user may apply a force to the waste tube 304 to slide a portion of the waste tube 304 beyond the gripping structures but large enough that the waste tube 304 does not fall out of the cartridge 302 once inserted, regardless of the angle at which the cartridge 302 is held.

The tubular central portion 308 includes one or apertures proximal to the second end 324 (e.g., an aperture 326) that function to expel air from the central elongated cavity that is displaced by the waste tube 304 when the waste tube 304 is inserted. In the illustrated design, two apertures are include on opposite sides of the tubular central portion 308 such that it is possible to see straight through the cartridge 302 when the waste tube is not inserted. Other implementations may have one or more differently shaped or placed apertures that provide the same or similar functionality.

A plunger mechanism 318 is affixed to the T-shaped body 320 and includes a stem 322 adapted to slide into the central elongated cavity through a second end 324 of tubular central portion 308 responsive to an applied external force that compresses a spring 328. For example, a user may place a thumb on the end of the plunger mechanism 318 while wrapping his/her index finger and middle finger of the same hand around flanges 312 and 314. While in this position, the user pushes the thumb toward the index and middle fingers (in the direction of arrow "A") to compress a spring 328 and slide the stem 322 into the central elongated cavity of the tubular central portion 308, which forcibly ejects the waste tube 304 from the first end 310 of the central elongated cavity.

Figure 4:
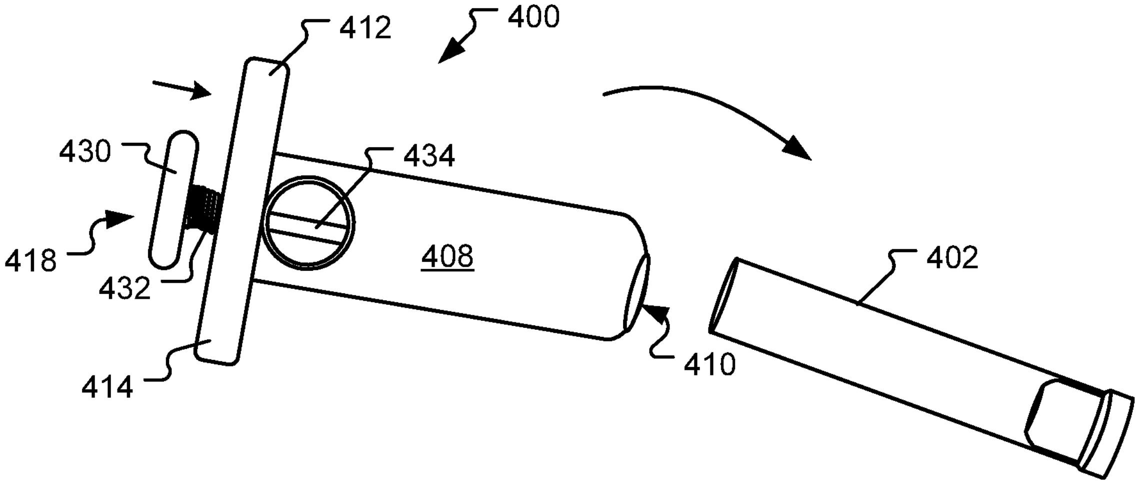
FIG. 4 illustrates touchless ejection of a waste tube from an exemplary cartridge that is used to hold and secure a waste tube during phlebotomy operations.

FIG. 4 illustrates touchless ejection of a waste tube 402 from an exemplary cartridge 400. The cartridge 400 may be understood as including features the same or similar to those shown and described with respect to FIG. 1-3 above including a tubular central portion 408, gripping flanges 412, 414, and a plunger mechanism 418. In FIG. 3, a base portion 430 of the plunger mechanism 418 has been pressed toward the tubular central portion 408 to compress a spring 432 and cause a stem 434 to slide into the central elongated cavity of the tubular central portion. Contact between the stem portion 434 and the waste tube 402 dislodges the waste tube 404 from the central elongated cavity such that the waste tube 404 is expelled out through an open end 410 of the cartridge 400 opposite the plunger mechanism 418.

According to one implementation, waste tube 402 can be easily inserted into the cartridge 400 (e.g., via single push of the waste tube 402 into the cartridge cavity) and touchlessly expelled from the cartridge 400, such as to drop the waste tube 402 into a biohazard collection box. Since the cartridge 400 remains entirely external to the waste tube, there is no potential for contamination of the cartridge 400 with the waste fluid that is collected within the waste tube 402 during a blood draw procedure. This ensures that the cartridge can be recycled without a need for extra sanitation operations. In some implementations, the stem 434 is not spring-loaded as described and shown in FIG. 1-4.

Figure 5:
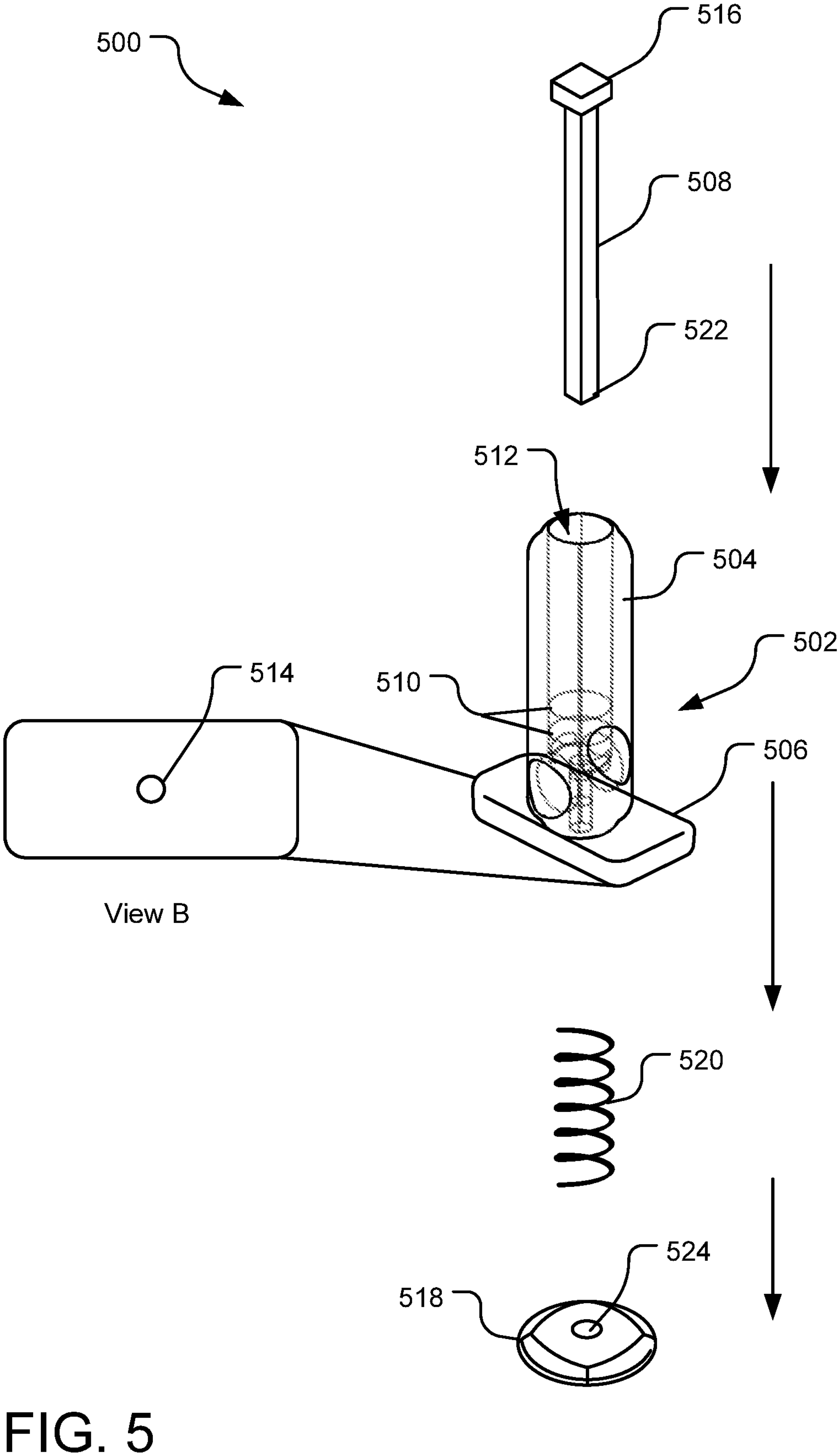
FIG. 5 illustrates example components of a cartridge for handling a waste tube with various components shown in an exploded view.

FIG. 5 illustrates example components of a cartridge 500 for handling a waste tube (not shown) with various components shown in an exploded view. The cartridge 500 includes a T-shaped central body 502 with a tubular central portion 504 having an internal elongated cavity 512 that receives a waste tube (not shown). In the implementation of FIG. 5, the tubular central portion 504 includes inwardly-protruding features 510, such as textured ribs, on an internal sidewall of the elongated cavity 512. When a waste tube is inserted into the elongated cavity 512, the waste tube slides dimensions are such that the waste tube slides easily until reaching the area with the inwardly-protruding features 510. The inwardly-protruding features locally narrow the diameter of the elongated cavity 512 so as to create an area of increased friction against the waste tube. To lock the waste tube within the elongated cavity 512, the user increases the force on the waste tube to overcome the friction and slide the waste tube beyond the textured ribs 510.

In some implementations, the cartridge 500 may be made of a more flexible material than the waste tube such that the user force applied to the waste tube causes the sidewalls of the elongated cavity 512 to flex away from the cartridge 500, allowing the cartridge 500 to slide past the inwardly-protruding features 510. Effectively, the textured ribs 510 lock the waste tube into place within the cavity 512 such that the waste tube may not be easily dislodged (e.g., fall out of) the elongated cavity 512 absent a user-applied ejection force.

The tubular central portion has a first end coupled to a flange piece 506 which forms a top of the "T" in the T-shaped central body 502. As shown in view B, the flange piece 506 has an aperture 514 through which a stem 508 may be threadedly inserted in the direction indicated by arrows in FIG. 5. The stem 508 has a first end 516 with a diameter larger than the diameter of the aperture 514 such that the stem 508 may be threaded through the aperture 514 and the first tip 516 remains, at all times, within the elongated cavity 508 (e.g., the stem cannot fall through the aperture 514 completely).

The flange piece 506 and provides gripping surfaces around which a user may wrap two fingers (e.g., index and middle finger) while positioning the thumb on a plunger mechanism, which may have characteristics the same or similar to the plunger mechanism 318 shown and described with respect to FIG. 3. The plunger portion is formed by the stem 508, a base 518, and a spring 520. Some implementations may not include the spring 520. The stem 508 threads through the aperture 514 and the spring 520 in the direction shown such that the spring 520 encircles the stem 508 and a second tip 522 of the stem 508 mates with the base 518 at a junction 524. In various implementations, the junction 524 may be secured in a variety of different ways including without limitation adhesives, soldering, welding, snap-joint (e.g., such that the stem 508 snaps into an aperture in the base 518), etc. Other components of the cartridge 500 not explicitly shown or described with respect to FIG. 5 may be the same or similar as other like-named components described elsewhere herein. Alternate implementations of the cartridge 500 may include features in addition to or in lieu of those shown.

Figure 6A:
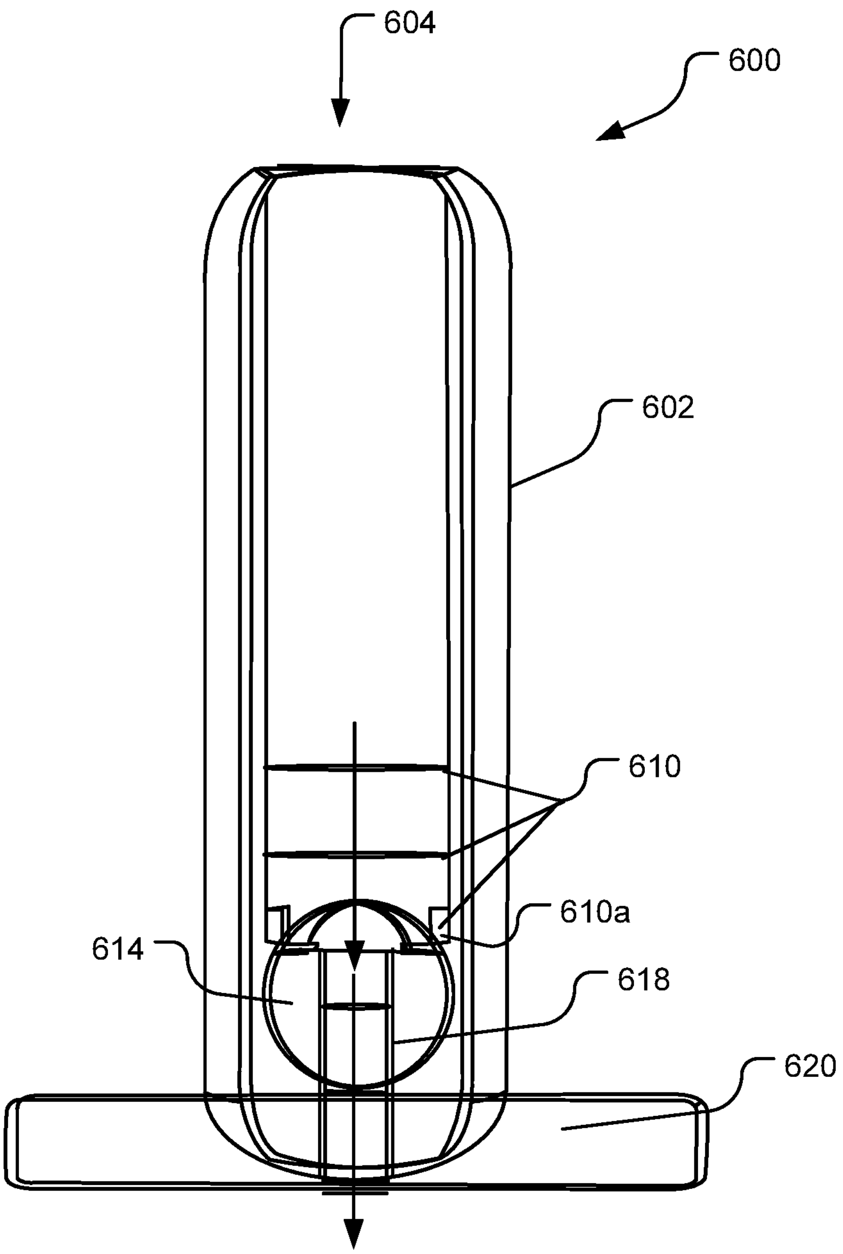
FIG. 6A illustrates a cross-sectional view of a T-shaped central body that may form part of a cartridge used for securing and positioning a waste tube during phlebotomy operations.

FIG. 6A illustrates a cross-sectional view of a t-shaped central body 600 that may form part of a cartridge used for securing and positioning a waste tube during blood draws. The T-shaped central body 600 has a tubular central portion 602 with an internal elongated cavity 604. In the implementation of FIG. 6, the tubular central portion 602 includes an internal sidewall with inwardly-protruding texture features 610 that provide friction, helping to secure the waste tube within the elongated cavity 604. The inwardly-protruding texture features 610 may be any shape and size (e.g., rib-like, grooves, bumps) so as to locally narrow the diameter of the elongated cavity 604 to be the same as or just smaller than a corresponding diameter of a waste tube received within the elongated cavity 604. In the illustrated implementation, a textured feature 610*a* narrows the elongated cavity enough that the waste tube cannot slide paste it. Thus, the textured feature 610*a* essentially forms a resting place upon which the end of the waste tube rests when it is fully inserted into the cavity 604.

The tubular central portion 602 further provides one or more through-holes 616 that provide a channel between the elongated cavity 604 and an environment external to the tubular central portion 602. In at least one implementation, the waste tube is designed to be just slightly smaller than the largest diameter of the elongated cavity 604 such air displaced cannot readily flow through the interface between the waste tube and the sidewall of the elongated cavity 604. Rather, the insertion of the waste tube into the elongated cavity 604 forces air out through the one or more through-holes 616. In one implementation, the diameter of the elongated cavity 604 is approximately 11.1 mm and the corresponding diameter of the waste tube is approximately 10.25 mm. Thus, the waste tube fits snugly within the elongated cavity 604. The waste tube may include internally-protruding features, such as textured ribs or teeth (as described elsewhere herein) to provide friction that effectively locks the waste tube into place. These features may locally reduce the internal diameter of the internal cavity to approximately match or to be less than the diameter of the waste tube.

In addition to those features discussed above, the tubular central portion 602 also includes a stem-guiding portion 618 for receiving and guiding a stem (such as the stem 508 in FIG. 5) through an aperture in a flange piece 620. The stem-guiding portion 618 includes a channel (illustrated by arrows) that fluidly couples the inside of the elongated cavity 604 with the environment external to the tubular central portion 602. Other features of the t-shaped central body 600 not specifically described with respect to FIG. 6 may be the same or similar to those described elsewhere herein.

Figure 6B:
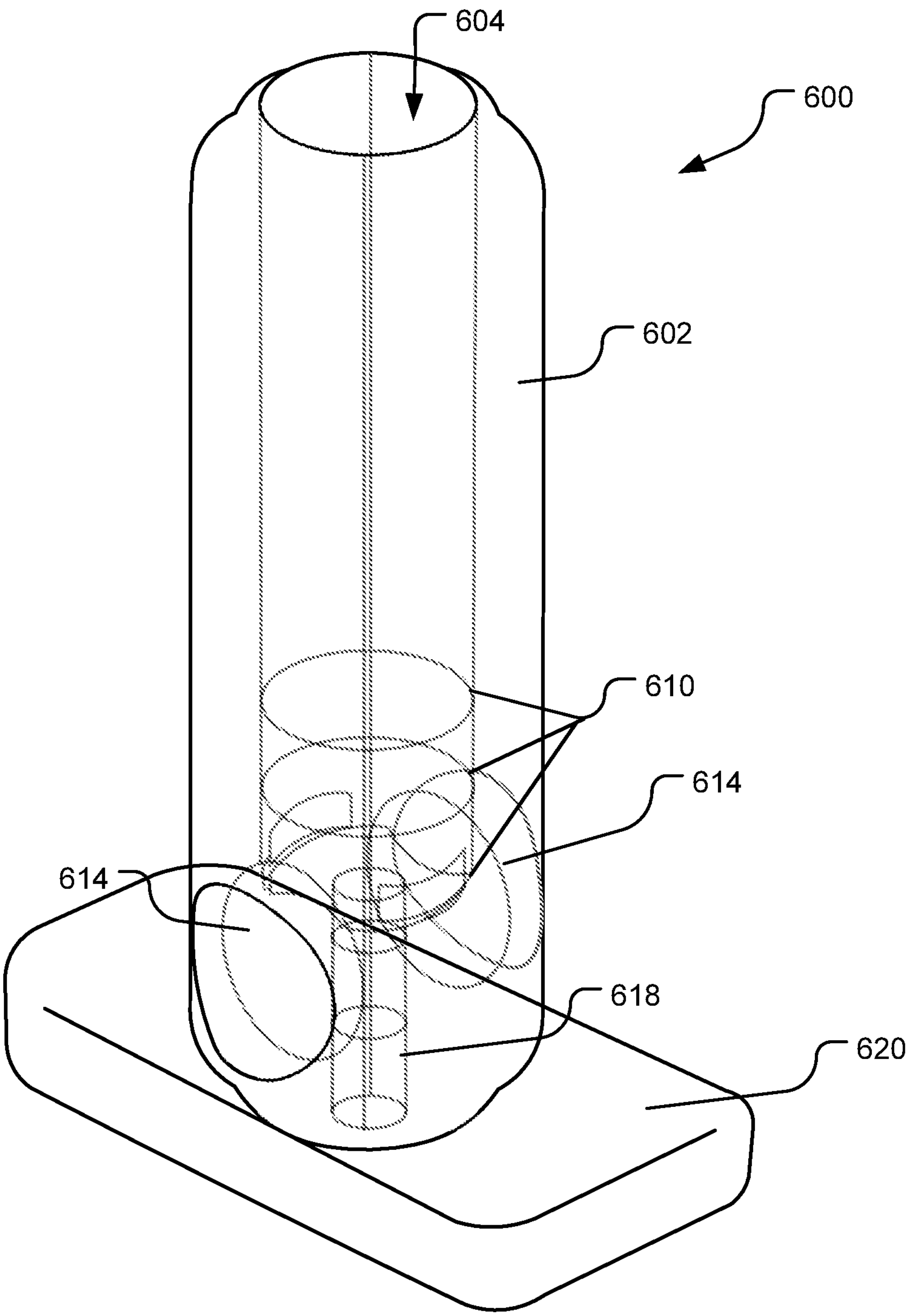
FIG. 6B illustrates a perspective view of the T-shaped central body shown in FIG. 6A.
Figure 7:
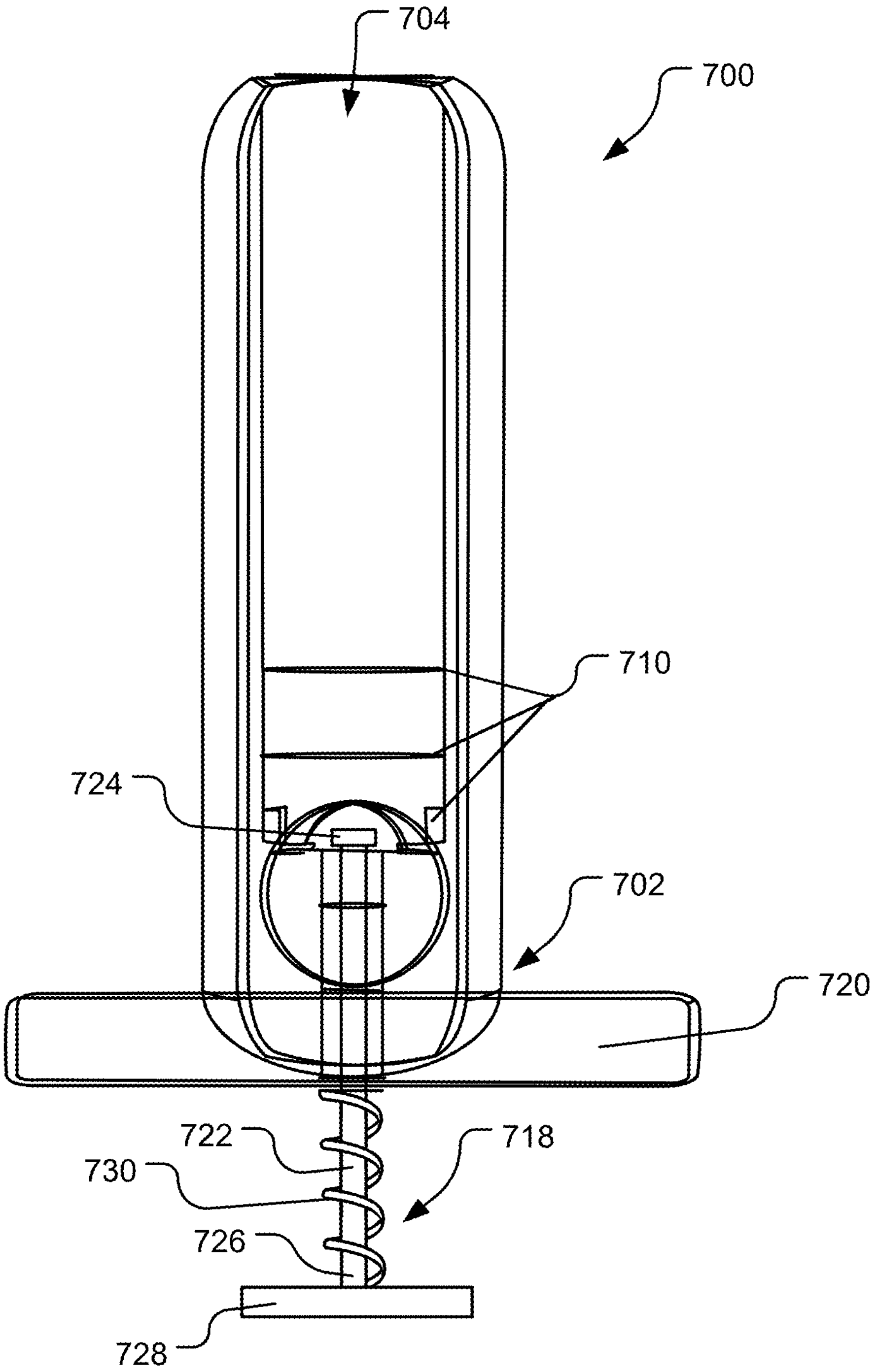
FIG. 7 illustrates another example cartridge used for handling a waste tube during phlebotomy operations.

FIG. 6B illustrates a perspective view of the T-shaped central body 600 shown in FIG. 6A. FIG. 7 illustrates another example cartridge 700 used for handling a waste tube during phlebotomy operations. The cartridge 700 includes T-shaped central body 702 with a tubular central portion 702 and internal elongated cavity 704 that receives a waste tube. Like the implementation of FIGS. 6-7, the T-shaped central body 702 includes an internal sidewall with inwardly-protruding texture features 710 that provide friction, helping to secure the waste tube within the elongated cavity 704.

In addition to those features discussed above and with respect to FIG. 6, the cartridge 700 further illustrates a plunger mechanism 718 coupled to the T-shaped central portion 702. The plunger mechanism 718 includes a stem 722 is threaded through a spring 730 and also through an aperture in a flange portion 720 such that a first end 724 of the stem 722 rests internal to the elongated cavity 704. The plunger mechanism 718 further includes a base 728 and a second opposite end 726 of the stem 722 is coupled to the base 728. Aspects of the cartridge 700 not specifically described with respect to FIG. 7 may be the same or similar to like-named components described elsewhere herein.

The above specification, examples, and data provide a complete description of the structure and use of exemplary embodiments of the invention. Since many implementations of the invention can be made without departing from the spirit and scope of the invention, the invention resides in the claims hereinafter appended. Furthermore, structural features of the different embodiments may be combined in yet another implementation without departing from the recited claims.

What is claimed is:

1. A system comprising:

a first needle;

a collection vial containing a liquid waste, the collection vial coupled to the first needle and to a first end of a tubing;

a hub assembly comprising:

a second needle with a first end coupled to a second end of the tubing attached to the collection vial; and a hub with a first end and a second end, wherein the first end of the hub includes the second needle and the second end of the hub is adapted to receive a waste tube with a hollow interior, wherein the waste tube couples to a second end of the second needle within the hub to create a vacuum-sealed channel between the collection vial and the waste tube, the hub assembly being configured to draw the liquid waste out of the collection vial, through the second needle, and into the waste tube as the collection vial receives a fluid sample through the first needle; and a cartridge for securing the waste tube within the hub during collection of the fluid sample, the cartridge comprising at least:

a tubular central body with an open first end and an elongated cavity, the elongated cavity being sized and shaped to receive the waste tube through the open first end; and a plunger mechanism affixed to the tubular central body, the plunger mechanism including a stem adapted to slide into the elongated cavity through a second end of the tubular central body responsive to an applied external force to eject the waste tube from the elongated cavity through the open first end of the tubular central body at a time when the hub assembly is decoupled from the waste tube.

2. The system of claim 1, wherein the cartridge further comprises:

one or more gripping flanges attached to the second end of the tubular central body, the one or more gripping flanges extending from the tubular central body in a plane substantially perpendicular to elongated cavity.

3. The system of claim 2, wherein a user ejects the waste tube from the cartridge by applying a first force to the gripping flanges and a second opposite force to the plunger mechanism than plunges the stem into the elongated cavity.

4. The system of claim 1, wherein the tubular central body is sized to rest within a center portion of the hub while contacting the hub about a circumference of the tubular central body.

5. The system of claim 1, wherein the plunger mechanism comprises a base portion attached to a first end of the stem external to the cartridge, the base portion providing a contact point at which the applied external force is applied to plunge the stem into the elongated cavity and eject the waste tube.

6. A method comprising:

inserting a waste tube with a hollow interior through a first open end of an elongated cavity formed in a tubular central body of a cartridge, the cartridge including a plunger mechanism affixed to the tubular central body, the plunger mechanism including a stem slidably threaded through an opening in a second end of tubular central body opposite the first open end;

while the waste tube is fitted within the elongated cavity of the cartridge, inserting the elongated cavity of the cartridge into a hub including a needle that provides a channel into the waste tube to support vacuum-sealed transmission of fluids between the waste tube and a fluid connection vial attached to the needle of the hub; and ejecting the waste tube from the elongated cavity through the first open end of the tubular central body by applying a force to a base portion of the plunger mechanism that forcibly slides a length of the stem into the elongated cavity and into contact with the waste tube.

7. The method of claim 6, wherein ejecting the waste tube through the first open end of the tubular central body further comprises:

applying a first force to one or more flanges attached to the second end of the tubular central body while simultaneously applying a second force to the base portion of the plunger mechanism, the second force being in a direction that is opposite the first force.

8. The method of claim 6, wherein the plunger mechanism includes a spring that is adapted to position a length of the stem external to the elongated cavity when the cartridge is at rest in the absence of the force, the spring collapsing under the force to slide the length of the stem into the elongated cavity to forcibly eject the waste tube from the cartridge.

9. The method of claim 6, wherein the stem of the plunger mechanism is threaded through a hole in the second end of the tubular central body such that the stem has a first end internal to the cartridge and a second end external to the cartridge, the first end of the stem having a diameter wider than a diameter of the hole such that the stem is prevented from sliding out the second end of the tubular central body.

10. The cartridge of claim 6, wherein the tubular central body of the cartridge further comprises a means for locking the waste tube within the elongated cavity.

11. The method of claim 10, wherein the means for securing the waste tube within the elongated cavity of the cartridge comprises:

one or more inwardly-protruding features formed on a sidewall internal to the elongated cavity, the one or more inwardly-protruding features locally narrowing a diameter of the elongated cavity to be smaller than a diameter of the waste tube such that the one or more inwardly-protruding features grip and secure the waste tube within the elongated cavity.

12. A system comprising:

a first needle;

a collection vial containing a liquid waste, the collection vial coupled to the first needle and to a first end of a tubing;

a hub assembly comprising:

a second needle with a first end coupled to a second end of the tubing attached to the collection vial; and a hub with a first end including the second needle and a second end adapted to receive a waste tube with a hollow interior that couples to a second end of the second needle within the hub to create a vacuum-sealed channel between the collection vial and the waste tube, the hub assembly being configured to draw the liquid waste out of the collection vial, through the second needle, and into the waste tube as the collection vial receives a fluid sample through the first needle; and a cartridge for securing the waste tube within the hub during collection of the fluid sample, the cartridge comprising at least a tubular central body with an open first end and an elongated cavity, the elongated cavity being sized and shaped to receive the waste tube through the open first end, wherein the cartridge is configured to receive an externally-applied force directed through a second end of the elongated cavity opposite to the open first end and transfer the applied force to the waste tube to forcibly eject the waste tube through the open first end of the tubular central body and out of the cartridge at a time when the hub is decoupled from the waste tube.

* * * * *